(12) United States Patent
Li et al.

(10) Patent No.: US 12,709,618 B2
(45) Date of Patent: Aug. 18, 2026

(54) METHOD FOR EFFICIENTLY EXTRACTING AND SEPARATING HIGH-PURITY TETRODOTOXIN FROM PUFFERFISH VISCERA

(71) Applicant: Zhongyang Biotechnology (Shanghai) Co., Ltd., Shanghai (CN)

(72) Inventors: Haihang Li, Shanghai (CN); Linlin Zhang, Shanghai (CN); Wenlong Zhang, Shanghai (CN); Junmei Zeng, Shanghai (CN); Zhiyong Chu, Shanghai (CN); Jianhua Ye, Shanghai (CN); Xiaoming Qian, Shanghai (CN)

(73) Assignee: Zhongyang Biotechnology (Shanghai) Co., Ltd., Shanghai (CN)

( * ) Notice: Subject to any disclaimer, the term of this patent is extended or adjusted under 35 U.S.C. 154(b) by 636 days.

(21) Appl. No.: 18/003,825

(22) PCT Filed: May 5, 2022

(86) PCT No.: PCT/CN2022/090917
§ 371 (c)(1),
(2) Date: Dec. 29, 2022

(87) PCT Pub. No.: WO2022/233298
PCT Pub. Date: Nov. 10, 2022

(65) Prior Publication Data

US 2023/0257391 A1 Aug. 17, 2023

(30) Foreign Application Priority Data

May 4, 2021 (CN) ........................ 202110487094.X

(51) Int. Cl.
*C07D 491/22* (2006.01)

(52) U.S. Cl.
CPC ........ *C07D 491/22* (2013.01); *C07B 2200/13* (2013.01)

(58) Field of Classification Search
CPC .......................... C07D 491/22; C07B 2200/13
See application file for complete search history.

(56) References Cited

U.S. PATENT DOCUMENTS 6,552,191 B1 * 4/2003 Zhou .................... C07D 491/18 544/247
2002/0060188 A1 5/2002 Zhou et al.

FOREIGN PATENT DOCUMENTS

CN 1470514 A 1/2004
CN 101317846 A 12/2008
(Continued)

OTHER PUBLICATIONS

Sasaki et al. Toxicon.2008;51(4):606-614 (Year: 2008).*
(Continued)

*Primary Examiner* — Clinton A Brooks
*Assistant Examiner* — Jerica Katlynn Wilson
(74) *Attorney, Agent, or Firm* — Wolf, Greenfield & Sacks, P.C.

(57) ABSTRACT

A method for extracting and separating high-purity tetrodotoxin (TTX) from pufferfish viscera, comprising the following steps: adding an acid alcohol homogenate to pufferfish viscera, adding a certain amount of a flow aid and stirring uniformly, loading into a chromatographic column, eluting with the same acidic alcohol, collecting an eluent containing TTX, and concentrating under reduced pressure to obtain a TTX concentrated solution; further separating using ion exchange resin column chromatography, collecting an eluent containing TTX, and using a nanofiltration membrane to perform concentration or reduced pressure evaporation to dryness to obtain a TTX crude product; and precipitating and
(Continued)

Pufferfish viscera
Extracting by homogenization and column chromatography extraction method
Extraction solution
Concentrating to water phase, and extracting to remove oil
Extract concentrated solution
Separating by ion exchange resin column chromatography, followed by membrane concentration, and vacuum drying
TTX crude product
Precipitation and crystallisation
TTX pure product crystallising the TTX crude product by means of a solvent to obtain TTX with a purity greater than 98%.

9 Claims, 2 Drawing Sheets

(56) References Cited

FOREIGN PATENT DOCUMENTS

| | | | |
|---|---|---|---|
| CN | 101891751 | A | 11/2010 |
| CN | 102584843 | A | 7/2012 |
| CN | 104311569 | A | 1/2015 |
| CN | 107880054 | A | 4/2018 |
| CN | 111117917 | A | 5/2020 |
| CN | 113321661 | A | 8/2021 |
| JP | 66010331 | B | 11/1964 |

OTHER PUBLICATIONS

Englard et al. Methods in Enzymology. 1990;182:285-300 (Year: 1990).*
International Search Report and Written Opinion for Application No. PCT/CN2022/090917 mailed on Jul. 15, 2022.
PCT/CN2022/090917, Jul. 15, 2022, International Search Report and Written Opinion.
Decision to Grant for Japanese Application No. 2023-523323, dated Aug. 20, 2024.
Notification to Grant Patent Right for Invention for Chinese Application No. 202110487094.X, dated Mar. 9, 2022.

* cited by examiner

METHOD FOR EFFICIENTLY EXTRACTING AND SEPARATING HIGH-PURITY TETRODOTOXIN FROM PUFFERFISH VISCERA

CROSS-REFERENCE TO RELATED APPLICATIONS

The present application is a national stage filing under 35 U.S.C. § 371 of international PCT application PCT/CN2022/090917, filed May 5, 2022, which claims the priority to the Chinese patent application with the filing No. CN 202110487094.X filed with the Chinese Patent Office on May 4, 2021, and entitled "Method for Efficiently Extracting, Separating and Preparing High-purity Tetrodotoxin from Pufferfish Viscera", the contents of each of which are incorporated herein by reference in entirety.

TECHNICAL FIELD

The present disclosure relates to the technical field of extraction, separation and purification of biologically active substances in animal bodies, and in particular, to a preparation method of tetrodotoxin from pufferfish viscera.

BACKGROUND

Tetrodotoxin (TTX) is originally a small-molecule and non-protein alkaloid with strong neurotoxin extracted from pufferfish. In 1909, Japanese scholar Tawara extracted crude toxin from pufferfish ovaries for the first time and named the same (Bane et al., 2014). In 1950, Yokoo obtained purified TTX crystals from *Takifugu rubripes* ovaries for the first time (Yokoo, 1950). In 1964, the molecular formula ($C_{11}H_{17}N_3O_8$) and the chemical structure of TTX were determined (Buchwald et al., 1964; Woodward and Gougoutas, 1964; Tsuda and Ikuma et al., 1964). Over a long period of time, tetrodotoxin was considered as a unique toxic substance in the body of pufferfish, and this had not been changed until American scientists Mosher et al. separated TTX from *Tarichatorosa* in 1964 (Mosher et al., 1964). Studies to date had shown that TTX not only exists in bodies of many kinds of pufferfishes, but also widely exists in nearly 140 kinds of animals, including vertebrates and invertebrates (Lorentz et al., 1016), such as gobies (Zhu Guoping, et al., 2015), newts (Yotsu-Yamashita et al., 2012), bivalves and gastropods (Laura et al., 2019), blue-ring octopus (Whitelaw et al., 2019), nemerteans (Vlasenko et al., 2018), nematodes (Mao Jie, et al., 2020), etc. Moreover, it had been found that many kinds of microorganism can produce TTX (Chau et al., 2011; Magarlamov et al., 2017).

TTX is one of the most toxic neurotoxins known, and its toxicity to humans is around 1200 times that of cyanide, and there is no known antidote (Lago et al., 2015). The $LD_{50}$ value of TTX to mice is 10 μg/kg (intraperitoneal), 16 μg/kg (subcutaneous), and 332 μg/kg (oral) (Kao, 1966). After ingestion of TTX by humans, the severity of poisoning symptoms is related to the dosage (Homaira et al., 2010). Initial symptoms include lingual and lip numbness (paresthesia), followed by headaches or vomiting, and muscular weakness and ataxia may be developed. In severe cases, death may be caused by respiratory failure or heart failure (Noguchi and Eebesu, 2001). The lethal dose of TTX to humans is 1.33 μg/kg (Kasteel and Westerink, 2017). The problems such as that TTX is transmitted by means of biological chain and a large number of marine and freshwater farmed animals contain TTX cause people to worry about and pay attention to the safety of environment.

TTX is a blocking agent of fast-voltage gated sodium channel, can cause nerve and muscular anesthesia, and can be medically used for local anesthesia and addiction-free analgesia of various patients with cancer and having under gone surgery, etc. As a local anesthetic (Ogura and Mori, 1968), TTX does not have obvious cardiovascular side effects (Butterworth, 2010; Stoetzer et al., 2016) or myotoxicity (Padera et al., 2006). Unlike local anesthetics commonly used clinically, TTX has a binding site located outside the membrane, and it can be used in combination with other local anesthetics to produce a synergistic effect (Kohane et al., 1998; Berde et al., 2011; McAlvin et al., 2015). Researchers also used the anesthetic property of TTX to treat various types of pains, such as severe cancer pains (Hagen et al., 2008; 2017), or relieve opioid withdrawal syndromes (Chen Suqing, et al., 2001; Kohane et al., 2003; Shi et al., 2009) and so on. In addition, researchers found that tumor growth is obviously reduced in carcinoma-bearing mice treated with TTX (El-Dayem et al., 2013). TTX can also inhibit the mobility or invasiveness of tumor cells, and prevent the metastasis of highly metastatic tumors and leukemias (Shan et al., 2014; Stock and Schwab, 2015). TTX is expected to be clinically applied in many fields.

TTX has a complex structure and is difficult to synthesize chemically. Although total artificial synthesis of TTX has been accomplished as early as in 2003 (Ohyabu et al., 2003), there are too many steps of artificial synthesis, 23-67 steps are required on average, and the obtained yield content is only 0.34%-1.82% (Chau and Cuyfikub, 2011; Makarova et al., 2019). Moreover, in the synthesis process, it is necessary to develop a series of purification methods. Therefore, it is difficult to achieve large-scale production by laboratory synthesis of TTX and analogs thereof (Chau and Cuyfikub, 2011; Bane et al., 2014; Makarova et al., 2019). Although many microorganisms can produce TTX, the yield is quite low (Lago et al., 2015), the mechanism of production thereof is unclear, and to improve its yield and to develop a purification method are both difficult problems to solve (Liu Yanting, et al., 2008). Thus, TTX extracted and prepared from animal tissues is currently the major source of TTX.

TTX is an aminoperhydroquinazoline compound (pKa 8.76), has a molecular formula of $C_{11}H_{17}N_3O_8$, a molecular weight of 319.27, and strong absorption at 190-200 nm, and contains a cage-shaped orthoester structure (Moczydlowski, 2013), as shown in FIG. 1. Almost all carbon atoms in the molecules thereof have an asymmetric substitution, and 1,2,3-guanidylamino and hydroxyl groups on C-4, C-9, and C-10 in the vicinity thereof are active groups. The TTX crystal is white in color and odorless, does not have a fixed melting point, and is gradually carbonized at 220° C. or above (Cui Jianzhou, et al., 2005), but does not melt even at 300° C. (Tsuda and Kawamura, 1952). Pure TTX is insoluble in water and most organic solvents, such as methanol, ethanol, and dimethyl sulfoxide, is easily dissolved in dilute acetic acid solution, and the activity thereof is easily destroyed in strong acid or strong alkaline solutions (Moczydlowski, 2013). TTX is positively charged in a neutral solution, and under weakly acidic condition, orthoester form, lactone form, 4-epi TTX, and 4,9-anhydro TTX coexist (Nishikawa and Isobe, 2013).

Formula 1

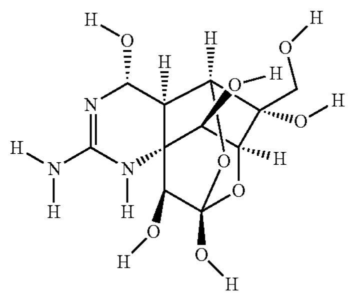

Structural Formula of Tetrodotoxin (TTX)

TTX has a unique structure and properties, and high-purity TTX can hardly be extracted, separated, purified, and prepared from biomaterials by conventional separation and purification methods for natural alkaloids (Makarova et al., 2019). Initially, Tawara (1909) separated TTX from aqueous extracts of pufferfish ovaries by a lead acetate precipitation method, but the purity was only 0.2%-4% (Moczydlowski, 2013). Despite many attempts, it was not until the early 1950s that Yokoo realized the preparation of pure crystalline TTX through alumina column chromatography and recrystallization after continuously treating crude tetrodotoxin with phosphotungstic acid, mercury picric acid, bitter ketonic acid, phenylhydrazine, etc. (Yokoo, 1950). Subsequently, Tsuda and Kawamura separated and purified TTX by taking 1000 kg of pufferfish ovaries as raw materials, through potato starch partitioning chromatography, activated carbon adsorption chromatography, and filter paper chromatography (Tsuda and Kawamura, 1952).

At present, a process of preparing TTX generally includes extracting pufferfish visceral tissues taken as raw materials, with an aqueous acetic acid solution as an extraction solvent, assisted by ultrasonic waves or/and heating. The extract is purified by cation exchange column chromatography-activated carbon column. TTX is precipitated through acid-dissolution and alkali-precipitation, and finally, the precipitated TTX is purified and recrystallized by preparative high performance liquid chromatography (HPLC). Main reports concerning the extraction and purification method of TTX are summarized in Table 2.

TABLE 2

Extraction and Purification Process for TTX Reported in Literatures

| Raw material | Extraction method | Separation and purification method | Purity | References |
|---|---|---|---|---|
| Pufferfish ovaries or/and livers | acid-water immersionextraction | microfiltration→ultrafiltration→nano-filtration→ reverse osmosis→HPLC preparation | >99% | Yi Ruizao, et al., 2002 |
| Pufferfish ovaries | immersionextractionby water or weak organic acid | Ambedite IRC-60 cation exchange column chromatography→activated carbon adsorption→crystallisation | >80% | Zhou and Shum, 2003 |
| Pufferfish livers | aqueous acetic acid solution with pH of 4.0, boiled to extract | D201 macroporous resin →Ambedite IRC-86 cation exchange resin column →ultrafiltration→sephadex G-10 purification→HPLC preparation →crystallisation | 99.5% | Cui Jianzhou, et al., 2005 |
| Pufferfish viscera | 50% aqueous ethanol solution (containing 0.1% acetic acid), boiled to extract | activated carbon column→D152 cation exchange column→Bio-GelP2 polyacrylamide molecular sieve chromatography→crystallisation | >80% | Su Jie, et al., 2010 |
| *Gastrophysus lunaris* ovaries | 0.1% aqueous acetic acid solution, ultrasonic-assisted extraction | D152 ion exchange resin→activated carbon →Bio-Gel P2 gel column chromatography | 46.6% | Huang Zhimei, 2010 |
| pufferfish roes or livers | ultrasonic water extraction | ion exchange→ ultrafiltration→ nanofiltration →HPLC preparation→ crystallisation | >99% | Wang Xiuju, et al., 2012 |
| Pufferfish viscera | immersionextractionby aqueous acetic acid solution | dialysis→reverse weak anion chromatography separation→cation exchange chromatography purification→freeze-drying | >80% | Yang Yuhui, 2015 |
| Pufferfish livers and ovaries | pure water immersionextraction | polymerized ferric sulfate flocculation→D152 cation exchange column chromatography→low pressure silica gel column chromatography→HPLC preparation→crystallisation | >99% | Zhong Xinjia, Liu Yandong, 2016 |
| Pufferfish viscera | aqueous acetic acid solution, heated to extract | activated carbon decolorization→ macroporous resin adsorption→cation exchange resin column chromatography → nanofiltration→ crystallisation | 99.5% | Zeng Junjie, et al., 2018 |
| *Nassariidae* | 1% acetic acid methanol solution, 60° C. waterbath and ultrasonic-assisted extraction | WCX solid phase extraction→D152 cationic resin→Sephadex G-10 purification →HPLC preparation | 32.6% | Sun Bolun, 2018 |

TABLE 2-continued

Extraction and Purification Process for TTX Reported in Literatures

| Raw material | Extraction method | Separation and purification method | Purity | References |
|---|---|---|---|---|
| *Gastrophysus* lunarisovaries and livers | 0.1% aqueous acetic acid solution, 40 ° C. waterbath and ultrasonic extraction | WCX weak cation exchange column → polyamide chromatographic column → freeze-drying → recrystallisation | >90% | Deng Xingchao, et al., 2018 |
| *Nassariidae* | acetic acid, methanol and ultrasonic water bath extraction | carbon-nanotube solid phase extraction →HPLC preparation | >99% | Zhao Donghao, et al., 2019 |
| Pufferfish viscera | Stirring and soaking in acetic-acid-containing alcohol-water mixed solution | activated carbon decolorization-macroporous adsorption resin purification→microfiltration → ultrafiltration→nanofiltration→ recrystallisation | 97-99% | Zhang Xiaojun, et al., 2020 |

However, these extraction and purification methods have problems in the following several aspects.

1) Low extraction efficiency. TTX can hardly be extracted from tissues and extracted completely, and the conventional soaking extraction or ultrasonic-assisted extraction methods have low extraction efficiency and require a large amount of extraction solvent.
2) Acidic water is mostly used as the extraction solvent, which results in a large amount of water-soluble substances such as proteins contained in the extract solution, so that the proteins need to be removed in the subsequent TTX separation and purification processes, and it is difficult to carry out separation and purification. Meanwhile, there are many separation and purification steps, such that the recovery rate is very low.
3) Most reports are limited to laboratory researches, and experimental methods and results are not verified, and can hardly be replicated and used for the production of TTX.

Therefore, it is quite important to develop a simple and efficient TTX extraction, separation, and purification method and process that can be used for mass production.

REFERENCES

Chen Suqing, Ren Leiming, Huang Zhiqiang. Effect of tetrodotoxin on naloxone-precipitated withdraw syndrome in morphine-dependent rats and mice. Chinese Journal of Pharmacology and Toxicology, 2001(06): 434-440.

Cui Jianzhou, Gong Qinglin, Gu Qianqun, et al. Studies on the preparation and purification of tetrodotoxin (TTX) by high performance liquid chromatography. High Technology Letters, 2005(4): 89-94.

Deng Xingchao, Huang Liansheng, Chen Huan, et al. Tetrodotoxin extraction and purification method: CN108586475A. 2018-09-28.

Huang Zhimei. Study on extraction, separation, and purification process of tetrodotoxin. Fujian Agriculture and Forestry University, 2010.

Liu Yanting, Lei Hongtao, Zhong Qingping. Trend on the study of tetrodotoxin. Food Research and Development, 2008(02): 156-160.

Mao Jie, Gong Xiaoling, Bao Baolong. Identification of TTX and *anisakis* parasites in *Takifugu xanthopterus* from the East China Sea. Journal of Shanghai Ocean University, 2020: 1-9.

Su Jie, Liu Zhiyu, Huang Zhimei. A research on tetrodotoxin purification. Journal of Fujian Fisheries, 2010(4): 56-59.

Sun Bolun. Study on extraction, purification, and preparation technologies of tetrodotoxininnassarius. Zhejiang Ocean University, 2018.

Tan Guili, Lin Guoyou. HPLC detection of tetrodotoxin. Enterprise Science and Technology & Development, 2011 (13): 26-28.

Wang Xiuju, Ding Yamin, Yin Zhiyong. Extraction method for high-purity tetrodotoxin: CN102584843A. 2012-07-18.

Yang Yuhui. Method for extracting and primarily purifying tetrodotoxin: CN104311569A. 2015-01-28.

Yi Ruizao, Xu Chen, Hong Zhuan, et al. Process for large-scale preparing tetrodotoxin high-purity monomer: CN1385431. 2002-12-18.

Zhang Xiaojun, Chen Si, Zeng Junjie, et al. Method for efficiently extracting tetrodotoxin: CN107641128B. 2020-03-17.

Zhong Xinjia, Liu Yandong. Method for preparing tetrodotoxin: WO2016061874A1. 2016-04-28.

Zeng Junjie, Zhang Xiaojun, Chen Si, et al. Method for preparing high-purify tetrodotoxin: CN107880054A. 2018-04-06.

Zhao Donghao, Wang Xufeng, Wang Qiang, et al. Preparing method for tetrodotoxin standard biological samples CN109142602A. 2019-01-04.

Zhu Guoping, Liao Jianmeng, Wu Bin, et al. The seasonal variation of tetrodotoxin in *Amoya caninus*. Marine Environmental Science, 2015, 34(01): 66-69.

Bane V, Lehane M, Dikshit M. Tetrodotoxin: chemistry, toxicity, source, distribution and detection. Toxins, 2014, 6(2): 693-755.

Berde C, Athiraman U, Yahalom B, et al. Tetrodotoxin-Bupivacaine-Epinephrine Combinations for Prolonged Local Anesthesia. Marine Drugs, 2011, 9: 2717-2728.

Buchwald H D, Durham L, Fischer H G, et al. Identity of tarichatoxin and tetrodotoxin. Science, 1964, 143(3605), 474-475.

Butterworth J F. Models and mechanisms of local anesthetic cardiac toxicity: a review. Regional Anesthesia and Pain Medicine, 2010, 35(2): 167-176.

Chau J, Ciufolin M A. The chemical synthesis of tetrodotoxin: An ongoing quest. Marine Drugs, 2011, 9: 2046-2074.

Chau R, Kalaitzis J A, Neilan B A. On the origins and biosynthesis of tetrodotoxin. Aquatic Toxicology, 2011, 104: 61-72.

El-Dayem S M A, Fouda F M, Ali E H A, et al. The antitumor effects of tetrodotoxin and/or doxorubicin on Ehrlich ascites carcinoma-bearing female mice. Toxicology and Industrial Health, 2013, 29: 404-417.

Hagen N A, Souich P D, Lapointe B, et al. Tetrodotoxin for moderate to severe cancer pain: A randomized, double blind, parallel design multicenter study. Journal of Pain and Symptom Management, 2008, 35: 420-429.

Hagen N A, Cantin L, Constant J, et al. Tetrodotoxin for Moderate to Severe Cancer-Related Pain: A Multicentre, Randomized, Double-Blind, Placebo-Controlled, Parallel-Design Trial. Pain Research & Management, 2017, 2017: 1-7.

Homaira N, Rahman M, Luby S P, et al. Multiple outbreaks of puffer fish intoxication in Bangladesh, 2008. The American Journal of Tropical Medicine and Hygiene, 2010, 83: 440-444.

Kohane D, Smith S, Louis D, et al. Prolonged duration local anesthesia from tetrodotoxin-enhanced local anesthetic microspheres. Pain, 2003, 104: 415-421.

Kohane D S, Yieh J, Lu N T, et al. A Re-examination of Tetrodotoxin for Prolonged Duration Local Anesthesia. Anesthesiology, 1998, 89, 119-131.

Kao C Y. Tetrodotoxin, saxitoxin and their significance in the study of excitation phenomena. Pharmacological Reviews, 1966, 18: 997-1049.

Kasteel E E J, Westerink R H S. Comparison of the acute inhibitory effects of Tetrodotoxin (TTX) in rat and human neuronal networks for risk assessment purposes. Toxicology Letters, 2017, 270: 12-16.

Lago J, Rodriguez L P, Blanco L, et al. Tetrodotoxin, an Extremely Potent Marine Neurotoxin: Distribution, Toxicity, Origin and Therapeutical Uses. Marine Drugs, 2015, 13: 6384-6406.

Laura B, Michael J B, Kirsty F S, et al. Tetrodotoxin in marine bivalves and edible gastropods: A mini-review. Chemosphere, 2019, 236: 1-10.

Lorentz M N, Stokes A N, Rößler D C, et al. Tetrodotoxin. Current Biology, 2016, 26(19): 870-872.

Magarlamov T Y, Melnikova D I, Chernyshev A V. Tetrodotoxin-Producing Bacteria: Detection, Distribution and Migration of the Toxin in Aquatic Systems. Toxins, 2017, 9(5):1-20.

Makarova M, Rycek L, Hajicek J, et al. Tetrodotoxin: History, Biology, and Synthesis. Angewandte Chemie International Edition, 2019, 58(51):18338-18387.

McAlvin J B, Yhang C, Dohlman J C. Corneal Anesthesia with Site 1 Sodium Channel Blockers and Dexmedetomidine. Investigative Ophthalmology & Visual Science, 2015, 56: 3820-3826.

Moczydlowski E G. The molecular mystique of tetrodotoxin. Toxicon, 2013, 63: 165-183.

Nishikawa T, Isobe M. Synthesis of Tetrodotoxin, a Classic but Still Fascinating Natural Product. The Chemical Record, 2013, 13: 286-302.

Noguchi T, Ebesu J S M. Puffer poisoning: Epidemiology and treatment. Toxin Reviews, 2001, 20: 1-10.

Ogura Y, Mori Y. Mechanism of local anesthetic action of crystalline tetrodotoxin and its derivatives. European Journal of Pharmacology, 1968, 3(1): 58-67.

Ohyabu N, Nishikawa T, Isobe M. First asymmetric total synthesis of tetrodotoxin. Journal of the American Chemical Society, 2003, 125(29): 8798-8805.

Padera R F, Tse J Y, Bellas E, et al. Tetrodotoxin for prolonged local anesthesia with minimal myotoxicity. Muscle Nerve, 2006, 34: 747-753.

Shan B, Dong M, Tang H, et al. Voltage-gated sodium channels were differentially expressed in human normal prostate, benign prostatic hyperplasia and prostate cancer cells. Oncology Letters, 2014, 8: 345-350.

Shi J, Liu T T, Wang X, et al. Tetrodotoxin reduces cue-induced drug craving and anxiety in abstinent heroin addicts. Pharmacology, Biochemistry and Behavior, 2009, 92: 603-607.

Stock C, Schwab A. Ion channels and transporters in metastasis. Biochimica et Biophysica Acta, 2015, 1848: 2638-2646.

Stoetzer C, Doll T, Stueber T, et al. Tetrodotoxin-sensitive α-subunits of voltage-gated sodium channels are relevant for inhibition of cardiac sodium currents by local anesthetics. Naunyn Schmiedebergs Archives of Pharmacology, 2016, 389: 625-636.

Tsuda K, Ikuma S, Kawamura M, et al. Tetrodotoxin. VII. On the structures of tetrodotoxin and its derivatives. The Pharmaceutical Society of Japan, 1964, 12, 1357-137.

Tsuda K, Kawamura M. The Constituents of the Ovaries of Globefish. VII. Purification of Tetrodotoxin by Chromatography (2). The Pharmaceutical Society of Japan, 1952, 72: 771-773.

Vlasenko A E, Velansky P V, Chernyshev A V, et al. Tetrodotoxin and its analogues profile in nemertean species from the sea of Japan. Toxicon: Official Journal of the International Society on Toxinology, 2018, 156: 48-51.

Whitelaw B L, Cooke I R, Finn J, et al. The evolution and origin of tetrodotoxin acquisition in the blue-ringed octopus (genus Hapalochlaena). Aquatic Toxicology (Amsterdam, Netherlands), 2019, 206: 114-122.

Wood S A, Taylor D I, McNabb P, et al. Tetrodotoxin concentrations in *Pleurobranchaea maculata*: Temporal, spatial and individual variability from New Zealand populations. Marine Drugs, 2012, 10: 163-176.

Woodward R B, Gougoutas J Z. The structure of tetrodotoxin. Journal of the American Chemical Society, 1964, 9, 49-74.

Yokoo A. Study on chemical purification of tetrodotoxin (3) purification of spheroidine. Journal of the Chemical Society, Japan, 1950, 71, 590-592.

Yotsu-Yamashita M, Gilhen J, Russell R W, et al. Variability of tetrodotoxin and of its analogues in the red-spotted newt, *Notophthalmus viridescens* (Amphibia: Urodela: Salamandridae). Toxicon, 2012, 59: 257-264.

Zhou M Q, Shum F H K. Method of extracting tetrodotoxin: U.S. Pat. No. 6,552,191B1. 2003-04-22.

SUMMARY

The present disclosure aims at providing a method for extracting, separating and preparing high-purity tetrodotoxin from pufferfish viscera with high extraction efficiency, low equipment investment, and convenient operations.

In order to achieve the above technical objectives, a technical solution used in the present disclosure is as follows:

a method for extracting, separating and preparing high-purity tetrodotoxin from pufferfish viscera, which includes the following steps:

(1) cutting fresh or thawed pufferfish visceral tissues into small pieces, adding a certain volume of acidic alcohol, and homogenizing the resultant in a homogenizer;

(2) adding a certain amount of a flow aid or a filter aid into a homogenate obtained in the above (1), stirring and mixing the resultant uniformly, and then loading the extract into a chromatographic column according to a column packing method of column chromatography; after standing for a certain period of time, eluting TTX in the materials successively by a column chromatography eluting method using the same acidic alcohol as above, measuring a TTX contents in the eluted fractions by HPLC until there is no TTX in the eluent, and collecting the TTX-containing eluent as a TTX extract solution;

(3) concentrating the TTX extract solution in the above (2) to a water phase under reduced pressure in a vacuum concentrator, recovering ethanol for reuse; and performing extraction on the water phase with an organic solvent to remove fat-soluble substances, where in the water phase obtained is a TTX extract concentrated solution;

(4) separating the TTX extract concentrated solution obtained in the above (3) by pre-treated ion exchange resin column chromatography, after sample loading, first eluting impurities with neutral ammonium salt and water successively, then eluting TTX with an acidic alcohol, collecting TTX-containing eluent, concentrating the TTX-containing eluent to a small volume by a nanofiltration concentrator, and then concentrating the same to dryness by a vacuum concentrator, to obtain a TTX crude product; and (5) subjecting the TTX crude product obtained in the above (4) to repeated acid-dissolution and alkali-precipitation or crystallisation multiple times with water and organic solvent, to obtain high-purity TTX. The purity of the TTX is 98% or higher upon HPLC analysis.

In some embodiments, in step (1), the pufferfish viscera are pufferfish ovaries or livers, after the ovaries or livers are cut into small pieces, 95% acidic alcohol with a volume 2.0 times the volume of the viscerais added, and the pufferfish visceral tissues are homogenized in a homogenizer.

In some embodiments, in step (2), the flow aid or the filter aid added in the homogenate is diatomite. The diatomite with a weight 0.5-1.0 times the weight of the viscera is added to the homogenate of the pufferfish visceral tissues, after they are uniformly stirred and mixed, the mixture is made to slowly flow into the chromatographic column. After standing for 1 hour, and all of the TTX in the materials is dissolved, the TTX therein is extracted by elution with 95% acidic alcohol until there is no TTX in the eluent.

In some embodiments, in step (3), the TTX extract solution is concentrated to a water phase under reduced pressure in a vacuum concentrator, and ethanol is recovered for repeated use. The water phase is extracted with an organic solvent to remove fat-soluble substances, and the water phase obtained is a TTX aqueous solution.

In some embodiments, in step (4), the TTX aqueous solution is separated by pre-treated or regenerated D-152 weakly acidic cation exchange resin column chromatography. After sample loading, impurities are eluted with neutral ammonium salt, pure water, a low-concentration acetic acid (0.1-1.0%) solution in sequence, and then the TTX is eluted with a 3-5% acetic acid solution.

In some embodiments, in step (5), the TTX eluent is concentrated to a small volume by a nanofiltration membrane concentrator with molecular weight cut-off of 100-300, and the concentrated solution is further evaporated to dryness by a vacuum concentrator. The concentrate obtained is eluted with alkaline alcohol and alkaline water to remove impurities, and then dissolved in acid water. The solution is adjusted to alkaline (pH 8-9), and crystallized in a 4° C. refrigerator to obtain the high-purity TTX.

Compared with the prior art, the present disclosure has following advantages.

1) For the preparation method of extraction and separation of TTX of the present disclosure, the extraction step therein adopts a novel, efficient and energy-saving column chromatography extraction method, and the extraction process is completed in one step, thus the extraction efficiency is higher. All of the TTX in the raw materials can be completely extracted with the extraction solvent having a volume 7 times that of the raw materials.

2) For the preparation method of extraction and separation of TTX of the present disclosure, the acidic high-concentration alcohol is used as the extraction solvent to perform column chromatography extraction, the extract solution has few water-soluble impurities and does not contain macromolecule water-soluble substances such as proteins, thus greatly simplifying the subsequent TTX separation and purification. Meanwhile, the extraction solvent can be recovered and reused.

3) The preparation method of extraction and separation of TTX of the present disclosure has a simple process, few steps, a high recovery rate of separation and purification, and a high overall yield of the TTX pure product. Therefore, the preparation cost of TTX is low.

4) The equipment used in the preparation method of extraction and separation of TTX of the present disclosure is common column chromatography and concentration equipment or the like, thus the equipment investment is very low.

5) For the preparation method of extraction and separation of TTX of the present disclosure, the extraction, separation and purification processes are all carried out at a room temperature; and the amount of the organic solvent is small, and the organic solvent can be recovered and reused, thus being energy-saving and environment-friendly.

BRIEF DESCRIPTION OF DRAWINGS

For ease of explanation, the present disclosure is described in detail by the following examples and accompanying drawings.

DETAILED DESCRIPTION OF EMBODIMENTS

Figure 1:
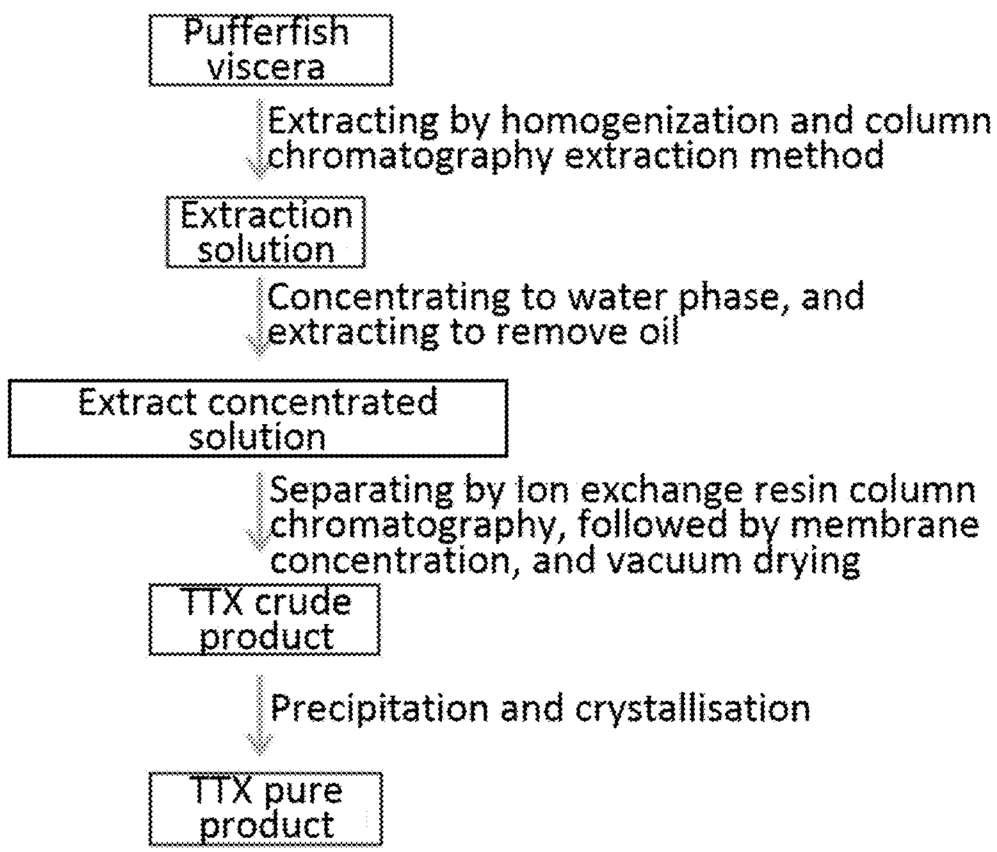
FIG. 1 shows a flow diagram of a process of extracting, separating, and preparing TTX of the present disclosure.

A process flow of the "method for efficiently extracting, separating and preparing high-purity tetrodotoxin from pufferfish viscera" of the present disclosure is as follows.

(1) 15 kilograms of pufferfish ovaries, after being rinsed with fresh water and undergoing impurity removal, were disintegrated by a meat grinder, acid (1% acetic acid), anhydrous ethanol having a weight 2-3 times that of the pufferfish ovaries and diatomite having a weight 0.6 times that of the pufferfish ovaries were added, the mixture was stirred uniformly, and uniformly loaded into a chromatographic column of ø 200×1500 mm, after standing for 1 hour, the mixture was eluted with acidic ethanol until there was no TTX in a chromatographic eluent. The chromatographic eluent, i.e., TTX extract solution, was collected. The extract solution containing TTX of 1236.0 mg was obtained, and TTX extraction yield was 96%.

(2) The TTX extract solution was concentrated to a water phase under reduced pressure, and the recovered ethanol can be used repeatedly. The concentrated solution was extracted with acetic ether having a volume 1/2-1/10 times that of the concentrated solution to remove low-polarity impurities and obtain a TTX extract concentrated solution. The extract concentrated solution containing TTX of 1168 mg was obtained, and a TTX recovery rate was 90.5%.

(3) The extract concentrated solution of 15 kilograms of pufferfish ovaries was separated by D-152 weakly acidic cation exchange resin column chromatography (ø 100×1000 mm). After sample loading, the sample was eluted at 3BV with a 0.2% ammonium phosphate solution, pure water, and 0.5% acetic acid water in sequence, such that impurities were washed away. Then, the resultant was eluted with a 2% aqueous acetic acid solution until there was no TTX, and the recovery rate of TTX was 93.6%. The eluent fractions with high TTX content were collected, concentrated to a small volume by nanofiltration, and concentrated to dryness under reduced pressure to obtain a TTX crude product, wherein the recovery rate of the TTX was 90.4%. An eluted phase with a low TTX content was then concentrated by D-152 weakly acidic cation exchange resin column chromatography to recover the TTX.

(4) The crude product was eluted 3 times with alkaline ethanol and alkaline water, and the precipitation was subjected to 3 times of acid-dissolution and alkali-precipitation repeatedly, to obtain purified TTX, wherein the recovery rate of TTX was 80.7%.

Figure 2:
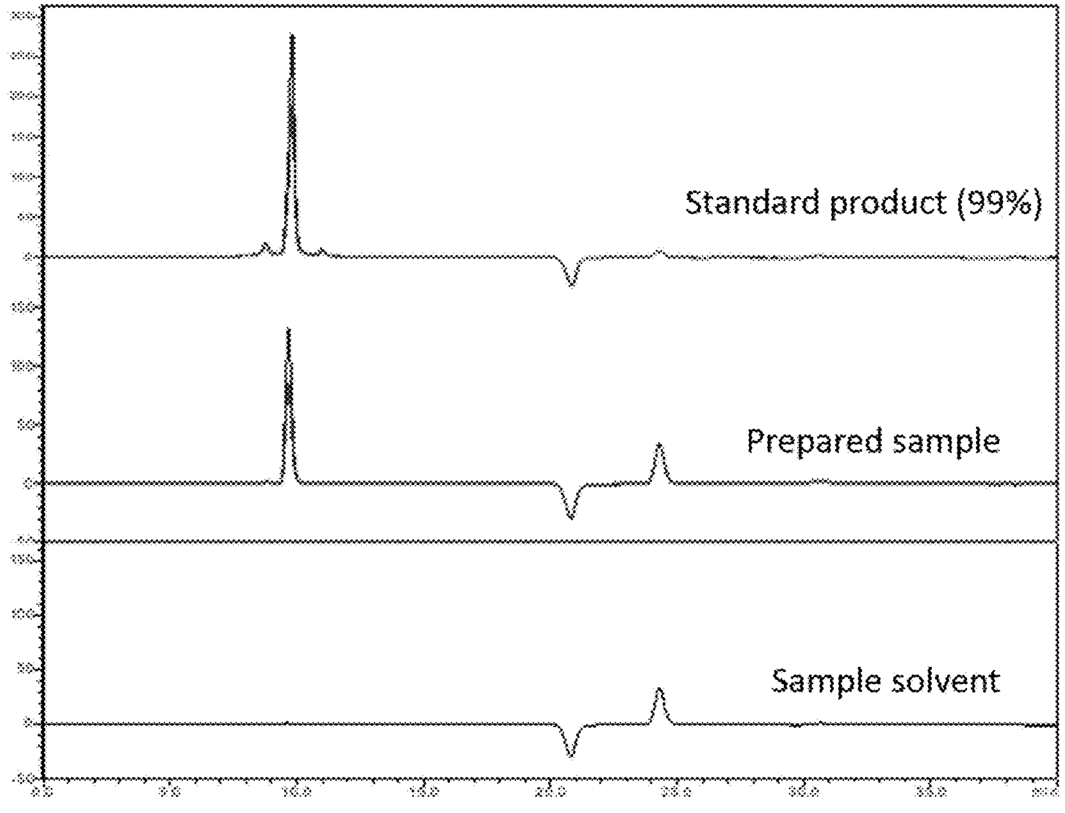
FIG. 2 shows HPLC analysis of a prepared TTX sample.

(5) The TTX was subjected to HPLC analysis and the content was measured, to obtain 815.6 mg of TTX. Upon HPLC analysis, the TTX purity was >98% (as in FIG. 2). The total recovery rate of TTX was 63.3%.

What is claimed is:

1. A method for efficiently extracting, separating and preparing tetrodotoxin from pufferfish viscera, comprising steps of:

(1) cutting fresh or thawed pufferfish visceral tissues into small pieces, adding acidic alcohol, and homogenizing a resultant in a homogenizer, wherein the acidic alcohol is a mixture of acetic acid and ethanol;

(2) adding a flow aid or a filter aid into a homogenate obtained in the (1), stirring and mixing a resultant uniformly, and then loading the resultant into a chromatographic column according to a column packing method of column chromatography; after standing, completely eluting tetrodotoxin (TTX) in materials by a column chromatography eluting method using the same acidic alcohol, measuring a TTX content in the eluent fractions by HPLC until no TTX exists in the eluent, and collecting the TTX-containing eluent fractions as an extract solution;

(3) concentrating the TTX extract solution in the (2) to a water phase under reduced pressure in a vacuum concentrator, recovering ethanol for repeated use, and performing extraction on the water phase with an organic solvent to remove fat-soluble substances, wherein a water phase obtained is a TTX extract concentrated solution;

(4) separating the TTX extract concentrated solution obtained in the (3) by pre-treated ion exchange resin column chromatography, after sample loading, first eluting impurities with neutral ammonium salt, pure water and low acidic solution successively, then eluting TTX with a higher acidic aqueous solution, collecting eluent phases having high TTX contents, and concentrating the TTX eluent phases by nanofiltration to dryness, to obtain a TTX crude product, wherein the nanofiltration comprises concentrating the TTX eluent separated by a cation exchange resin column chromatograph by a nanofiltration membrane, and the nanofiltration concentration membrane is a nanofiltration member with molecular weight cut-off of 100-200 Dalton; and (5) subjecting the TTX crude product to repeated acid-dissolution and alkali-precipitation or crystallisation multiple times in an aqueous solution or organic solvent, to obtain high-purity TTX, wherein a purity of the TTX is 98% or higher upon HPLC analysis.

2. The method for efficiently extracting, separating and preparing tetrodotoxin from pufferfish viscera according to claim 1, where in the step (1), the pufferfish viscera are tetrodotoxin-containing pufferfish ovaries, livers, or skins.

3. The method for efficiently extracting, separating and preparing tetrodotoxin from pufferfish viscera according to claim 1, where in the acidic alcohol in the step (1) is ethanol more than 50%.

4. The method for efficiently extracting, separating and preparing tetrodotoxin from pufferfish viscera according to claim 1, wherein the flow aid or filter aid in the step (2) is a substance for improving fluidity of a liquid in an animal tissue homogenate, including diatomite, perlite, and acidic clay, sawdust, cellulose, and activated carbon, and an added amount is 0.5-2.0 times a weight of the pufferfish viscera.

5. The method for efficiently extracting, separating and preparing tetrodotoxin from pufferfish viscera according to claim 1, where in the step (2), the flow aid is added to the homogenate, and column packing after the uniform stirring and mixing, impurity elution, and TTX elution methods and processes are carried out completely according to a method of column chromatography.

6. The method for efficiently extracting, separating and preparing tetrodotoxin from pufferfish viscera according to claim 1, wherein in the step (3), the TTX extract solution is concentrated to the water phase under reduced pressure at 65° C. in the vacuum concentrator, and recovered ethanol is repeatedly used for extraction of the TTX.

7. The method for efficiently extracting, separating and preparing tetrodotoxin from pufferfish viscera according to claim 1, wherein in the step (3), the water phase is extracted with the organic solvent to remove the fat-soluble substances, and the water phase obtained after the extraction is the TTX extract concentrated solution.

8. The method for efficiently extracting, separating and preparing tetrodotoxin from pufferfish viscera according to claim 1, wherein in the step (4), the extract concentrated solution is separated by the pre-treated ion exchange resin column chromatography, and the ion exchange resin is D-152 weakly acidic ion exchange resin.

9. The method for efficiently extracting, separating and preparing tetrodotoxin from pufferfish viscera according to claim 1, wherein in the step (5), an acid in the acid-dissolution and alkali-precipitation or crystallisation of the TTX crude product is acetic acid or phosphoric acid of 1%; and a base is ammonia water, with a pH value of 7-10.

* * * * *